United States Patent [19]
Mallet et al.

[11] Patent Number: 6,153,647
[45] Date of Patent: Nov. 28, 2000

[54] METHOD FOR AUGMENTING THE INOTROPIC EFFECTS OF β-ADRENERGIC AGONISTS USING PYRUVATE THERAPY

[75] Inventors: Robert T. Mallet, Arlington; James L. Caffrey, Burleson; Maria Isabel Tejero-Taldo, Cedar Hill, all of Tex.

[73] Assignee: My-Tech, Inc., Beverly Hills, Calif.

[21] Appl. No.: 09/190,814

[22] Filed: Nov. 12, 1998

[51] Int. Cl.[7] .................................................. A61K 31/22
[52] U.S. Cl. ........................ 514/546; 514/540; 514/557; 514/653
[58] Field of Search .................... 514/557, 546, 514/540, 653

[56] References Cited

U.S. PATENT DOCUMENTS

| | | | |
|---|---|---|---|
| 4,048,335 | 9/1977 | Lucchesi | 424/329 |
| 5,294,641 | 3/1994 | Stanko | 514/540 |
| 5,667,962 | 9/1997 | Brunengraber et al. | 435/1.2 |

OTHER PUBLICATIONS

Tejero–Taldo et al., Journal of Mol. and Cell. Cardiol., (1997), vol. 29, No. 6, pp. A202.

Tejero–Taldo et al., Journal of Mol. and Cell. Cardiol., (1998), vol. 30, No. 11, pp. 2327–2339.

Tejero–Taldo et al., FASEB Journal, (1996), vol. 10, No. 3, pp. A320.

*Primary Examiner*—Marianne M. Cintins
*Assistant Examiner*—C. Delacroix-Muirheid
*Attorney, Agent, or Firm*—Charles D. Gunter, Jr.; Kevin M. Kaulkner

[57] ABSTRACT

A method for treating medical patients suffering from cardiac trauma by co-administering pyruvate with a β-adrenergic agonist. This method for treating cardiac trauma, such as ischemic reperfusion injury and heart failure, augments the inotropic effects of β-adrenergic agents. Typical β-adrenergic agonists are epinephrine, norepinephrine, dobutamine, and isoproterenol. The amount of β-adrenergic agonist necessary to achieve a 50 percent increase of cardiac power is diminished five-fold when co-administered with pyruvate. Since high concentrations of agonists have many detrimental and hazardous side effects in patients, this invention would have important applications in the treatment of patients with cardiac trauma such as ischemia reperfusion injury.

8 Claims, 3 Drawing Sheets

METHOD FOR AUGMENTING THE INOTROPIC EFFECTS OF β-ADRENERGIC AGONISTS USING PYRUVATE THERAPY

BACKGROUND OF THE INVENTION

1. Field of the Invention

This invention relates to a method for augmenting the inotropic effects of β-adrenergic agonists by co-administering adequate concentrations of pyruvate. The primary target of action for this invention is in stunned or ischemic cardiac tissue. While β-adrenergic agonists are potentially useful in the treatment of inadequate cardiac function in patients, the high concentrations necessary cause undesirable side effects. The use of pyruvate decreases the amount of β-adrenergic agonist necessary to promote stimulation of the cardiac tissue, while decreasing the loss of energy reserves in the muscle, and decreasing oxidative damage to the muscle tissue.

2. Description of the Prior Art

Pyruvate has been recognized as a useful agent in the treatment of patients suffering from cardiac trauma. Stanko (U.S. Pat. No. 5,294,641) teaches a use of pyruvate in patients who suffer from cardiac trauma. The pyruvate may be a pre-treatment to anticipated surgery or administered during surgery. The object of the Stanko invention is to administer pyruvate to increase the cardiac output of a patient in need thereof without concurrently increasing the cardiac oxygen demand of the patient. Others have also disclosed the use of pyruvate in increasing the inotropic function of stunned myocardium. See Bunger et al., Eur. J. Biochem. 180 (1989): 221–233; Mallet et al., Biochim. Biophys. Acta 1224 (1994): 22–32.

Pyruvate has been shown to act as an antioxidant. This could also account for some of the useful characteristics of pyruvate in treating ischemia reperfusion injury. As an α-keto acid, pyruvate can directly react with $H_2O_2$ and lipid peroxides to neutralize these reactive species. Constantopoulos et al., Anal. Biochem. 139 (1984): 353–358. Also, pyruvate can be carboxylated by malic enzyme to generate four-carbon intermediates of the TCA (tricarboxylic acid) cycle, which are converted to citrate by reaction with acetyl CoA. Hiltunen et al., Biochim. Biophys. Acta 678 (1981): 115–121. Russell et al., Am. J. Physiol. 261 (1991): H1756–H1762. Citrate, in turn, can inhibit glycolytic metabolism of glucose, and diverts glucose metabolism to the hexose monophosphate pathway. The malic enzyme reaction and the hexose monophosphate pathway generate nicotinamide adenine diphosphate (NADPH), which reacts with oxidized glutathione disulfide (GSSG) to generate reduced glutathione (GSH), the principle intracellular antioxidant.

A derivative of pyruvate, a pyruvate thiolester, was disclosed by Brunengraber et al. (U.S. Pat. No. 5,667,962) for use in preventing reperfusion injury. Its action in the patient is mostly characterized as an antioxidant, thus diminishing the damaging effects of reactive oxygen species upon ischemia reperfusion.

Likewise, Lucchesi (U.S. Pat. No. 4,048,335) discloses a use of catecholamine derivatives in the inhibition of ischemia reperfusion injury in cardiac tissue. Others have also disclosed the direct use of catecholamines to stimulate function of injured heart muscle. Becker et al., J. Am. Coll. Cardiol. 7 (1986): 580–589; Ellis et al., Am Heart J. 107 (1994): 13–19.

The drawback to the prior inventions is their inability to facilitate the naturally beneficial effects of catecholamines on traumatized heart for clinical uses. Prior disclosures teach only that either pyruvate (Stanko) alone or catecholamines and their chemical derivatives (e.g., Lucchesi) alone can be used to treat inadequately functioning heart. The use of catecholamines and other β-adrenergic agonists alone would be most beneficial, but has the drawback of eliciting deleterious side effects in the patient. On the other hand, use of pyruvate alone, while improving some clinical aspects of ischemic injury, does not have the ideal inotropic effect of a β-adrenergic agonist. Thus, it is desirable to include the benefits of both in a cooperative manner to improve treatment of cardiac trauma.

It is the object of this invention to co-administer β-adrenergic agonists with pyruvate or its derivatives in patients suffering from cardiac trauma. The use of the agonist with pyruvate decreases the amount of agonist necessary to stimulate cardiac contractility, while increasing the energy reserves in the cardiac tissue as well as protecting the tissue from oxidative damage.

SUMMARY OF THE INVENTION

The object of this invention is to provide a method for augmenting the inotropic effects of β-adrenergic agonists. More generally, the object is to increase the sensitivity of human hearts to catecholamines, one of many β-adrenergic agonists. One important inotropic effect that the β-adrenergic agents exert is to make the heart more contractible, thus lowering the energy necessary for its natural function. The other major inotropic effect that agonists exert on the heart is to increase the heart rate.

While the term "pyruvate" has been used in the specification text and examples, those skilled in the art will understand that the term can encompass the traditional form of the commercially available compound (pyruvic acid, or 2-oxopropanoic acid, is $C_3H_4O_3$) as well as modifications and derivatives thereof.

This method would be beneficial to patients who suffer from heart ailments such as ischemia reperfusion injury. In that instance, the cardiac muscle is damaged in part because of an extended lack of oxygen, followed by a perfusion of oxygen, which results in an oxidative burst. Highly reactive oxygen radicals are produced from this oxidative burst, and the cardiac tissue can be damaged as a result. This damage lowers the heart's sensitivity to β-adrenergic agonists, thus reducing the favorable inotropic effects that agonists exert on the heart.

The method of augmenting the inotropic effect of agonists in this invention involves the co-administration of pyruvate with the agonist. If a preselected amount of pyruvate is administered to a patient along with the desired β-adrenergic agonist, for example, isoproterenol, the cardiac muscle becomes more sensitive to the effects of the agonist, requiring less of the agonist to achieve the desired effect. For example, without the addition of pyruvate it would take 5.2 nanomolar isoproterenol (a β-adrenergic agonist) in ischemically injured guinea-pig heart to achieve a 50 percent improvement of function of the heart. But, with the co-administration of 5 millimolar pyruvate it takes only 1.1 nanomolar isoproterenol to produce the same effect.

The co-administration of pyruvate with agonist can be accomplished by intravenous administration into the patient's coronary arteries. The pyruvate/agonist therapy has several benefits. First, the amount of β-adrenergic agonist necessary to increase the contractility of the heart is greatly diminished. This is important because: (1) low amounts of β-adrenergic agonists that do not inflict damage are ineffective in ischemically injured heart muscle, which is less responsive to these agents than healthy heart muscle; and (2) large quantities of β-adrenergic agonist can be detrimental due to adverse side effects in the patient.

Other beneficial effects of the combined pyruvate-β-adrenergic agonists therapy include prevention of the depletion of adenosine triphosphate (ATP) and other energy sources in the cardiac muscle, thus increasing the energy reserves in the heart. Also, oxidative damage may be directly mitigated by pyruvate since it can act as an antioxidant. Finally, even when higher doses of β-adrenergic agonist are necessary, the presence of the pyruvate maintains the level of ATP in the cardiac muscle and mitigates against the prooxidant effects of catecholamines. Häggendal et al., Acta Physiol. Scand. 131 (1987): 447–452; Singal et al., Can. J. Physiol. Pharmacol. 60 (1982): 1390–1397; Persoon-Rothert et al., J. Mol. Cell. Cardiol. 21 (1989): 1285–1291.

The above as well as additional objects, features, and advantages of the invention will become apparent in the following detailed description.

DETAILED DESCRIPTION OF THE INVENTION

Figure 1:
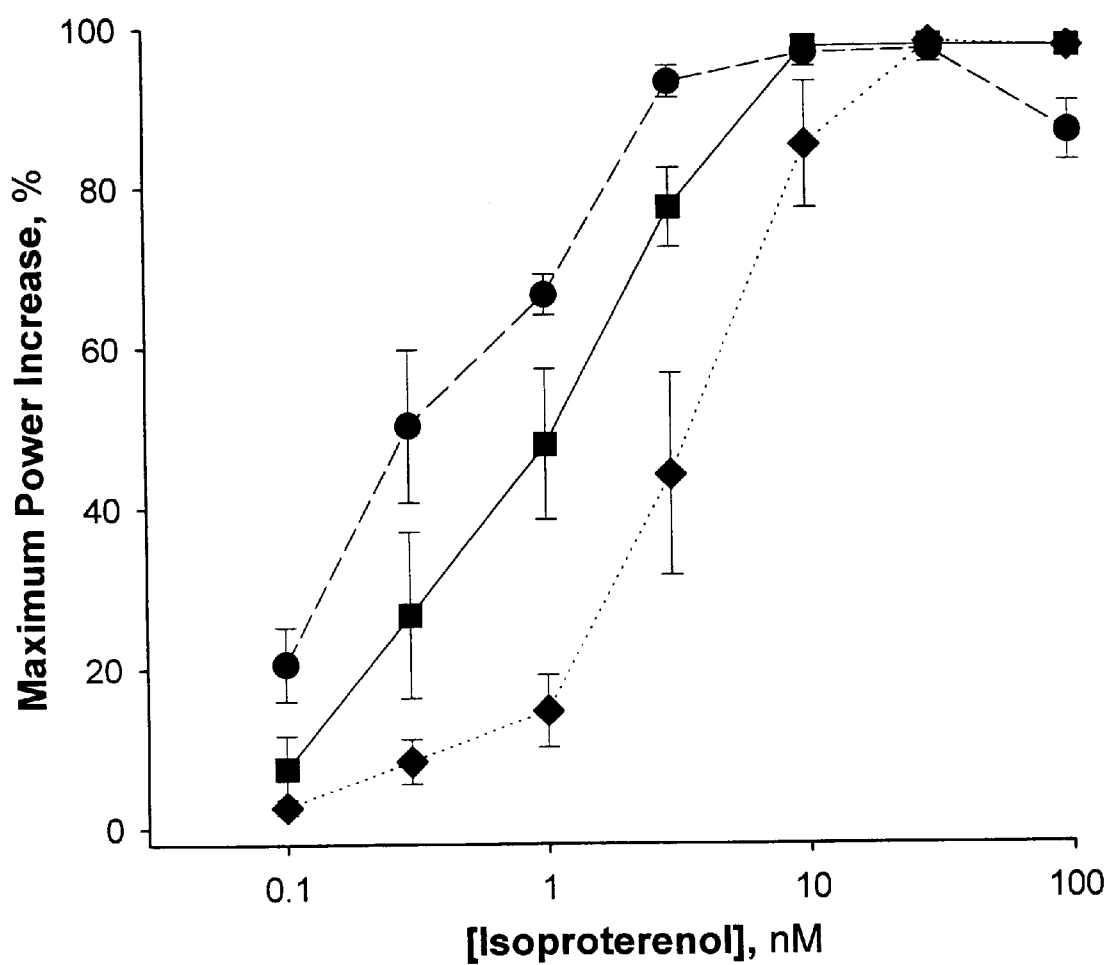
FIG. 1 is a graphical representation of the increase in cardiac power versus the concentration of isoproterenol in reperfused guinea-pig heart muscle.

Certain surgical procedures and diseases involving the heart (cardiac muscle tissue) are accompanied by trauma to the heart, especially ischemia. Ischemia injury results from a diminution or complete blockage of blood flow to the cardiac tissue, thereby depriving the tissue of oxygen and metabolic fuels, followed by the reperfusion of the tissue with oxygenated blood. This ischemia reperfusion trauma to cardiac muscle causes a decrease in contractile strength of the cardiac muscle, thus decreasing the performance of the heart.

Ischemia reperfusion injury is one of many types of cardiac trauma. There are also other injuries associated with the heart including acute heart failure, post-operative recovery following heart surgery, and cardiogenic, hypovolemic, or septic shock. β-adrenergic agonists, a major class of which include catecholamine, could potentially be used to provide support for inadequately functioning or failing heart due to the foregoing scenarios.

Catecholamines, including epinephrine (adrenaline), norepinephrine (noradrenaline), dobutamine, and isoproterenol act as β-adrenergic agonists in exerting inotropic influences on cardiac muscle. The major inotropic influences of these agonists is to increase the contractility of cardiac muscle, and stimulate heart rate. These agonists stimulate cardiac function by activating β-adrenergic signaling mechanisms in cardiac muscle cells. These adrenergic agonists are powerful inotropic agents and are potentially useful interventions for treatment of cardiac trauma or inadequate function in patients.

There are, however, important disadvantages to the use of adrenergic agonists to stimulate cardiac function. Potentially lethal cardiac arrhythmias and cardiac necrosis can result due to an imbalance between nutritional supply and energy demand when adrenergic agonists are used in patients. Specifically, adrenergic agonists produce disproportionate increases in cardiac energy requirements relative to increases in function, especially at higher doses, and deplete energy reserves of post-ischemic, failing cardiac muscle. The depletion of the energy reserves is characterized by a decrease in levels of ATP and the free energy of ATP hydrolysis, used to transfer free energy between energy-producing and energy consuming systems within virtually all living organisms.

The harmful effects of using adrenergic agonists may serve to worsen cardiac trauma. In order to avoid the deleterious effects of the agonists, lower concentrations must be used. However, these low dose levels are often ineffective in stimulating the heart. Thus, there is a need for a method of increasing the sensitivity of the heart to adrenergic agonists.

The purpose of this invention is to increase the potency of β-adrenergic agonists in cardiac muscle, thus allowing reduction of the applied dose of β-adrenergic inotropic agonists, such as catecholamines, necessary to restore function of ischemically injured or failing heart muscle. By increasing the potency of the agonists, the deleterious or toxic effects of high concentrations of the adrenergic agonists are avoided.

Co-administration of an adequate amount of pyruvate increases the potency of β-adrenergic agonists. Pyruvate, a natural fuel for the cardiac muscle, increases contractile function while preserving the energetics in patients suffering cardiac trauma. The cellular mechanisms for this metabolic inotropism include (a) the antioxidant effects of pyruvate, either by directly neutralizing $H_2O_2$, or by increasing the key intracellular antioxidant, reduced glutathione (GSH), (b) increasing the free energy of ATP hydrolysis, thus increasing the overall energetics of ATP activity, (c) increasing ATP production, and (d) elevating the TCA (tricarboxylic acid) cycle intermediates, which are generated by malic enzyme-catalyzed carboxylation of pyruvate. Russell et al., Am. J. Physiol. 261 (1991): H1756–H1762. Through one or a combination of these mechanisms, pyruvate restores the β-adrenergic responsiveness of stunned cardiac tissue.

In one embodiment of the invention, a sterile aqueous solution of 150 millimole sodium pyruvate in distilled water is prepared. The pH of the pyruvate solution is adjusted to 7.4 and the solution is filtered (0.45 micrometer pore) under vacuum. This pyruvate solution is administered to the patient's coronary arteries to produce a plasma pyruvate concentration of 4–6 millimolar. The agonists, catecholamine or other compounds that act as β-adrenergic agonists, are then administered while the pyruvate infusion is maintained.

This embodiment has been tested in guinea-pig hearts using isoproterenol as the agonist. In that procedure, the effectiveness of the pyruvate/isoproterenol co-administration was measured by the change in the $EC_{50}$, the amount of isoproterenol necessary to achieve a 50% restoration in cardiac power after stunning the heart. The $EC_{50}$ value of uninjured, non-ischemic heart is 0.3+/−0.06 nanomolar. For ischemically stunned heart the $EC_{50}$ value is 5.2+/−1.86 nanomolar without pyruvate. Pyruvate (5 millimolar) largely restored the cardiac tissue sensitivity to isoproterenol, lowering $EC_{50}$ to 1.1 +/−0.34 nanomolar. Thus, there was almost a 5-to-1 increase in sensitivity of the guinea-pig heart to isoproterenol when pyruvate is co-administered.

These results are described in detail in FIG. 1. FIG. 1 shows that pyruvate potentiates inotropic responses to isoproterenol in ischemically injured, reperfused cardiac muscle of guinea-pig. The data were obtained between 90 and 120 minutes of perfusion in uninjured time control hearts (circles), and between 30 and 65 minutes reperfusion following ischemia in untreated (diamond) and pyruvate treated (squares) stunned hearts. Pyruvate treatment was initiated at minutes of reperfusion. The increase in cardiac power ($EC_{50}$) is expressed as a percentage of the difference between pre-isoproterenol baseline and maximum isoproterenol effect. Baseline and maximum power (mJ $min^{-1}$ g $wet^{-1}$) were 107+/−33 and 266+/−42, respectively, in time control hearts; 19+/−6 and 329 +/−30 in untreated stunned hearts; and 39+/−5 and 348 +/−8 in pyruvate treated stunned hearts. The isoproterenol:power dose:response relationship was shifted to the right (in the graph) in stunned versus control hearts; thus, the stunned hearts were less responsive to isoproterenol and required higher, more hazardous doses of the β-adrenergic agonist to produce a given increase in cardiac power. Pyruvate treatment of stunned hearts shifted the relationship leftward (in the graph), toward the control curve (circles); thus, pyruvate lessened the dose of agonist necessary to produce a given increase in $EC_{50}$.

Furthermore, pyruvate potentiated the effects of submaximal doses of isoproterenol without depleting the cellular energy reserves. The effects of 5 millimolar pyruvate were examined in hearts stimulated with 30 nanomolar isoproterenol, which raises cardiac power to its normally observed maximum level. The pyruvate did not further enhance the inotropic response of stunned heart under these conditions, but did alleviate the energy (ATP) depleting effects of administering β-adrenergic agonist alone. These results indicate that pyruvate not only ameliorates the deleterious energetic effects of β-adrenergic stimulation, but also permits a reduction in the concentration of β-adrenergic agonist necessary for clinical efficacy in treating cardiac trauma.

Figure 2:
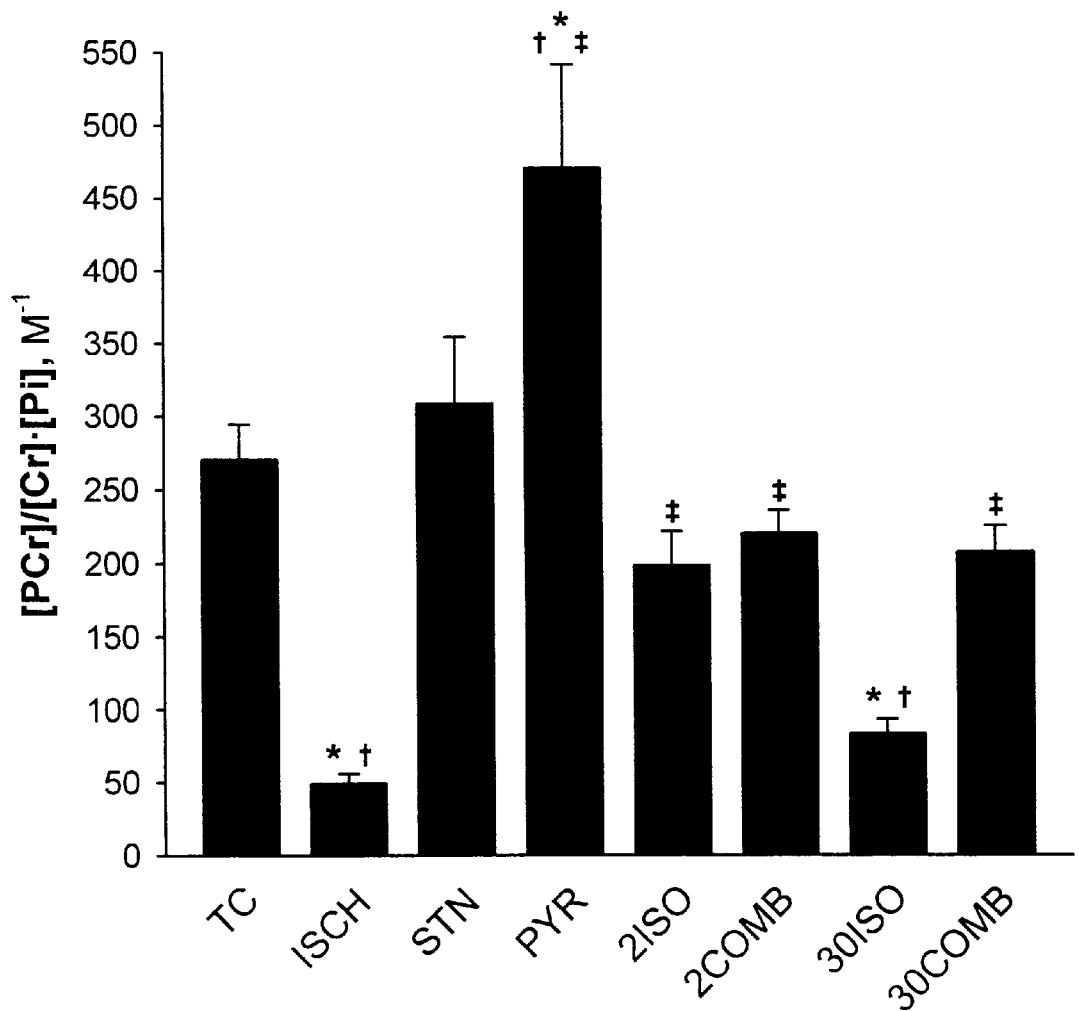
FIG. 2 is a graphical representation of the data showing the effects of pyruvate and the isoproterenol on cardiac energy reserves.

The effects of pyruvate and isoproterenol on cardiac energy reserves are depicted in FIG. 2. The energy level of cardiac muscle was assessed by measurement of phosphocreatine phosphorylation potential, i.e., the ratio of intracellular concentration of phosphocreatine ([PCr]) to the concentrations of its breakdown products creatine ([Cr]) and inorganic phosphate ([$P_i$]). The PCr potentials were measured in the following groups of hearts in 6 to 12 experiments per group: non-ischemic time control (TC), ischemia without reperfusion (ISCH), hearts stunned (STN) following ischemia and reperfusion without further treatment, stunned hearts treated with 5 millimolar pyruvate (PYR), stunned hearts treated with a low concentration (2 nanomolar) of isoproterenol (2ISO), hearts treated with the combination of 2 nanomolar isoproterenol and 5 millimolar pyruvate (2COMB), hearts stimulated with a high concentration (30 nanomolar) of isoproterenol (30ISO), and hearts treated with the combination of 5 millimolar pyruvate and 30 nanomolar isoproterenol (30COMB).

The data in FIG. 2 indicate that cardiac energy reserves were depleted during ischemia but recovered to the control level following reperfusion. Also, pyruvate increased the energy reserves in post-ischemic stunned hearts, whereas isoproterenol depleted energy reserves in a dose-dependent manner. In hearts stimulated by 2 nanomolar isoproterenol, pyruvate greatly increased contractile function without depleting energy reserves. Finally, in hearts stimulated by 30 nanomolar isoproterenol, pyruvate prevented depletion of energy reserves without lowering cardiac function.

The co-administration of pyruvate with β-adrenergic agonist also has antioxidant activity important in its function. In stunned guinea-pig hearts, treatment with 5 millimolar pyruvate plus 2 nanomolar isoproterenol at 15 to 30 minutes after reperfusion increased the level of reduced glutathione (GSH). Glutathione is a strong reducing agent in biological systems and is a natural cellular defense against oxidative damage as a result of such injuries as ischemia-reperfusion in cardiac muscle. Harlan et al., J. Clin. Invest. 73 (1984): 706–713; Kehrer et al., Free Rad. Biol. Med. 17 (1994): 65–75. Thus, a high ratio of GSH to GSSG indicates high levels of intracellular antioxidant reserves in cardiac muscle, and is desirable to ameliorate the effects of such insults to the heart as ischemia-reperfusion. In the present invention, the ratio of GSH to oxidized glutathione disulfide (GSSG) increased from 8.5+/−1.3 in the absence of pyruvate and isoproterenol to 26+/−2 when pyruvate and isoproterenol were added to stunned hearts.

Figure 3:
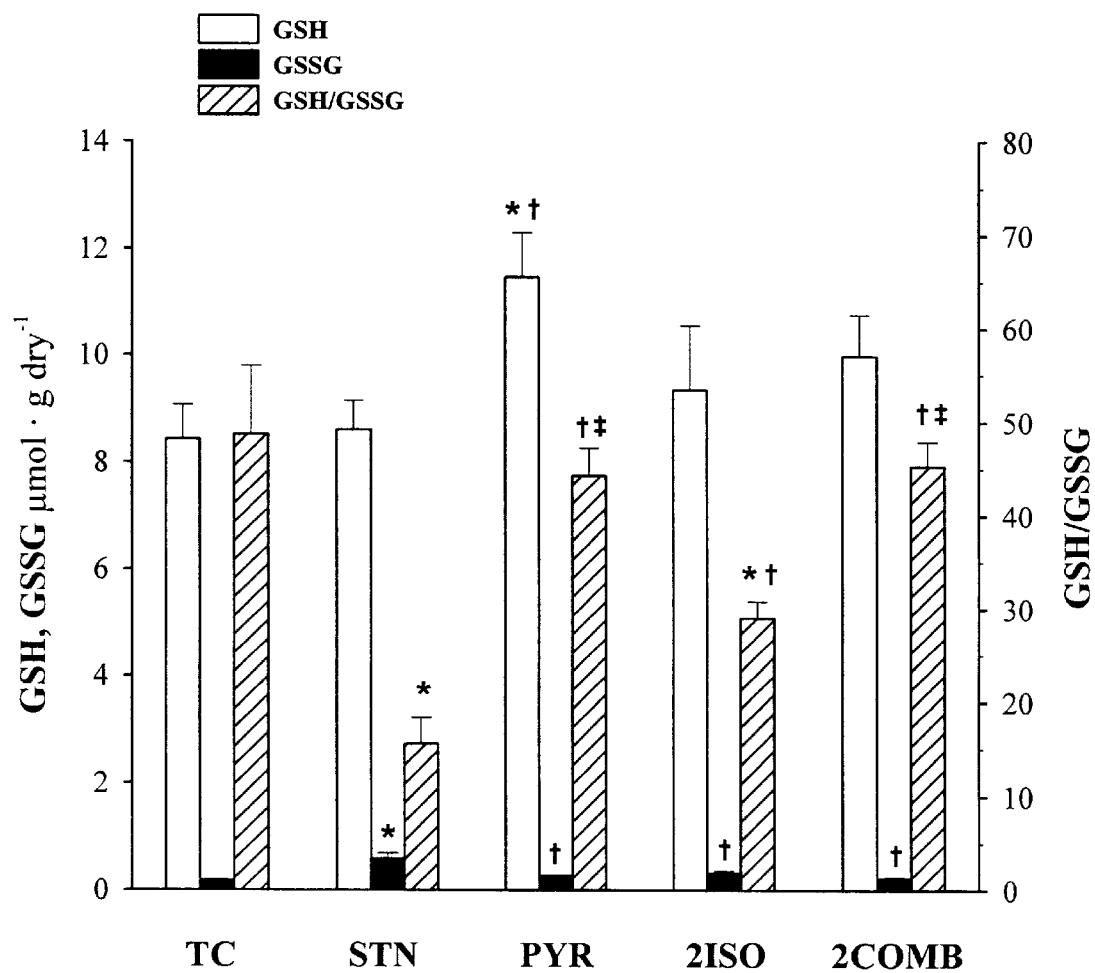
FIG. 3 is a graphical representation of the data showing the effects of pyruvate and isoproterenol on antioxidant metabolites in stunned heart muscle.

The beneficial antioxidant effects of the present invention are shown in the data in FIG. 3. Reduced glutathione (GSH) is the most important natural antioxidant in cardiac muscle. The ratio of GSH content to that of its oxidized product, glutathione disulfide (GSSG) is a measure of the availability of antioxidant defenses in the heart. Glutathione compounds were measured in non-ischemic time control hearts (TC), untreated post-ischemic stunned hearts (STN), and in stunned hearts treated with 5 millimolar pyruvate (PYR), 2 nanomolar isoproterenol (ISO) or the combination of pyruvate and isoproterenol (2COMB). GSSG content increased and the GSH/GSSG ratio fell 65% in stunned hearts relative to time controls, indicating depletion of cardiac antioxidant reserves. Pyruvate restored GSSG content and the GSH/GSSG ratio to respective time control levels. The GSH/GSSH ratio remained partially depressed in hearts treated with isoproterenol alone, but pyruvate restored antioxidant defenses in isoproterenol-treated hearts.

By co-administering pyruvate with β-adrenergic agonists, the full benefits of treating cardiac trauma with agonists can be realized. β-adrenergic drugs could potentially be used to provide inotropic support for inadequately functioning or failing heart in a variety of clinical scenarios, including management of acute heart failure, post-operative recovery following heart surgery or coronary revascularization, and treatment of low cardiac output associated with cardiogenic, hypovolemic or septic shock. In these settings, heart muscle retains its ability to respond to the agonists, and the co-administration of pyruvate greatly enhances this response.

The present invention is beneficial in decreasing the risk of cardiac arrhythmias which could occur when large doses of β-adrenergic agonist drugs are administered. Another benefit is the increase of cellular phosphorylation potential which is necessary to offset the potentially deleterious cardiac energy depletion by catecholamine. Also, co-administration of pyruvate could ameliorate the hazardous oxygen wasting effects of high concentrations of β-adrenergic agonists and, thus, improve cardiac mechanical efficiency by combination of its energizing effect and a reduction of the dosage of the agonist drug required to optimize post-ischemic cardiac function.

While the invention has been shown in only one of its forms, it is not thus limited but is susceptible to various changes and modifications without departing from the spirit thereof.

What is claimed is:

1. A method for augmenting the inotropic effects of β-adrenergic agonists comprising co-administering to a patient effective amounts of pyruvate and β-adrenergic agonists, wherein an amount of agonist is administered to the patient, the amount being less than what is otherwise required without the co-administration of pyruvate.

2. The method for augmenting the inotropic effects of β-adrenergic agonists of claim 1, wherein an amount of approximately 5 millimolar pyruvate is administered to the patient, decreasing the amount of agonist necessary to reach 50 percent cardiac power capacity.

3. The method for augmenting the inotropic effects of β-adrenergic agonists of claim 1, wherein the agonist and pyruvate are administered intravenously to the patient's coronary arteries.

4. The method for augmenting the inotropic effects of β-adrenergic agonists of claim 1, wherein co-administration of pyruvate with the agonist maintains a level of ATP energy reserves in the patient's cardiac muscle, where said agonist is administered to produce its maximum stimulation of cardiac performance.

5. A method for treating patients suffering from the effects of cardiac trauma which comprises treatment of the patient with effective amounts of pyruvate and β-adrenergic agonists, wherein an amount of β-adrenergic agonist is administered to the patient, the amount being less than what is otherwise required without co-administration of pyruvate.

6. A method for treating patients suffering from the effects of cardiac trauma in claim 5, wherein an amount of approximately 5 millimolar pyruvate is administered to the patient, decreasing the amount of β-adrenergic agonist necessary to reach 50 percent cardiac power capacity in the patient.

7. A method for treating patients suffering from the effects of cardiac trauma in claim 5, wherein the β-adrenergic agonist is administered intravenously to the patient's coronary arteries.

8. A method for treating patients suffering from the effects of cardiac trauma in claim 5, wherein co-administration of pyruvate with β-adrenergic agonist maintains a desirable level of ATP energy reserves in the patient's cardiac muscle, where said agonist is administered to produce a maximum stimulation of cardiac performance.

* * * * *